United States Patent [19]

Sugiura

[11] Patent Number: 5,928,606
[45] Date of Patent: Jul. 27, 1999

[54] DEVICE AND METHOD FOR CLEANING AND DISINFECTING CONTACT LENS USING WATER-ABSORBING SOLID SOFT MATERIAL CARRYING DISINFECTANT

[75] Inventor: Makoto Sugiura, Gifu, Japan

[73] Assignee: Tomey Technology Corp., Japan

[21] Appl. No.: 08/935,660

[22] Filed: Sep. 23, 1997

[30] Foreign Application Priority Data

Sep. 24, 1996 [JP] Japan .................................. 8-250760

[51] Int. Cl.⁶ ..................................................... A61L 2/00
[52] U.S. Cl. ........................ 422/28; 206/205; 206/316.1; 422/292; 422/294; 422/300; 424/409; 514/839
[58] Field of Search .............................. 422/28, 292, 294, 422/300; 134/901; 206/204, 205, 316.1; 424/409, 414; 514/839, 840

[56] References Cited

U.S. PATENT DOCUMENTS 3,063,083  11/1962  Obitts .
4,187,574  2/1980  Wrue ...................................... 15/104.92
4,559,662  12/1985  Kunold, Jr. ............................ 15/104.94
4,655,957  4/1987  Chromecek et al. ............... 252/174.23
5,071,276  12/1991  Nielsen et al. ................................ 401/9

FOREIGN PATENT DOCUMENTS

52-109953  9/1977  Japan .
62-153217  7/1987  Japan .
63-59960  3/1988  Japan .

*Primary Examiner*—Krisanne Thornton
*Attorney, Agent, or Firm*—Parkhurst & Wendel, L.L.P

[57] ABSTRACT

A device for cleaning and disinfecting a contact lens, including a treating portion which is brought into contact with the contact lens, wherein at least the treating portion is formed of a water-absorbing solid soft material to which a disinfectant is fixed, and a method of disinfecting a contact lens comprising the steps of: preparing the device for disinfecting the contact lens; impregnating at least the treating portion of the device with a wetting agent; and contacting the contact lens with the treating portion such that a surface of the contact lens to be disinfected is brought into contact with and held by the treating portion.

24 Claims, 4 Drawing Sheets

DEVICE AND METHOD FOR CLEANING AND DISINFECTING CONTACT LENS USING WATER-ABSORBING SOLID SOFT MATERIAL CARRYING DISINFECTANT

BACKGROUND OF THE INVENTION

1. Field of the Invention

The present invention relates to a device for cleaning and disinfecting a contact lens, and more particularly to a device for cleaning and disinfecting the contact lens that exhibits an excellent disinfecting or sterilizing effect while assuring a sufficiently high degree of safety with respect to the eyes of the user. The present invention is also concerned with a method of disinfecting the contact lens by using the disinfecting device.

2. Discussion of the Related Art

The contact lens worn on the eye of the user is likely to be soiled with stains such as proteins and lipids which are included in the tear fluid. These stains adhering to the contact lens not only deteriorate the wearing comfort of the contact lens as felt by the user, but also lower the eyesight of the user and cause various troubles to the eye such as hyperemia of the conjunctiva. Further, microorganisms such as bacteria adhering to the surface of the contact lens may proliferate thereon while the contact lens is stored after it is removed from the eye of the user. Such microorganisms may cause infectious diseases, giving adverse influences on the eye of the user.

In view of the above, the contact lens needs to be treated for cleaning and disinfection on a regular basis for safe and comfort wearing thereof. In general, the contact lens is treated in the following manner. Initially, the contact lens which was removed from the eye is rubbed with a cleaning agent including a surface active agent, to thereby remove lipid stains deposited on the surfaces of the contact lens. If it is desired to remove protein stains, the contact lens is soaked in a cleaning agent including a proteolytic enzyme so as to remove the protein stains. After the contact lens is rinsed with a rinsing liquid, the contact lens is accommodated and stored in a container filled with a storing liquid. Since the microorganisms tend to adhere to and proliferate on the lens surfaces, especially where the contact lens is a water-containing or hydrogel lens, such a water-containing or hydrogel contact lens needs to be disinfected by boiling. Namely, the hydrogel contact lens accommodated in a container requires a boiling procedure using a suitable boiling apparatus, in addition to the above-described procedure.

Thus, the procedure for treating the contact lenses is cumbersome, requiring several kinds of liquid agents such as a cleaning liquid and a storing liquid, and a suitable apparatus for boiling the contact lenses. Accordingly, it is troublesome and costly for the contact lens users to treat the contact lenses.

For solving the above-described problem, there are proposed some methods for treating the contact lens in a simplified manner at a relatively low cost. These methods permit the contact lens to be treated by using a single liquid agent which is obtained by adding, to the storing liquid, a surface active agent, a protein removing agent, and a disinfectant. In these proposed methods, the contact lens is disinfected not by a thermal disinfecting method which requires the above-described boiling apparatus, but by a chemical disinfecting method using a disinfectant. Thus, the proposed methods eliminate the conventionally required boiling operation using the exclusive apparatus for boiling the contact lens, so as to facilitate the procedure for treating the contact lens.

The above-described contact lens liquid agent functions not only as a disinfectant which has a chemical disinfecting effect, but also as a storage liquid. Such a contact lens liquid agent is required to exhibit a high degree of sterilizing effect, and at the same time, a low degree of toxicity with respect to the eyes, since the contact lens is soaked in the liquid agent for a relatively long period of time.

As the disinfectant used in commercially available chemical disinfecting agents for the contact lens, thimerosal, chlorhexidine or quaternary ammonium salt (e.g., benzalkonium chloride) is used. In JP-A-52–109953, JP-A-62–153217 and JP-A-63–59960, there are proposed a disinfectant or liquid agent for contact lenses, which includes benzalkonium chloride in an amount of 0.001–0.2%, and a disinfectant for soft contact lenses, which includes chlorhexidine in an amount of 0.01–0.05%.

Although these methods assure the user of easy treatment of the contact lens, these methods are not always favorable since the disinfectant gets into the eye. Recently, it is reported that such a disinfectant functions as an allergy intensifier and gives harm to the eyes of the user. Further, the disinfectant is adsorbed on or stored in the contact lens over a long period of use. For example, corneal troubles may be caused due to emission of the highly condensed disinfectant from the contact lens to the eye during wearing of the contact lens, or due to direct contact of the eye with the contact lens on which the disinfectant is adsorbed with high concentration ("Journal of Japan Contact Lens Society" in No. 34:267–276, 277–282, 1992, No. 35:219–225, 1993, No. 36:57–61, 1994, and No. 37:35–39, 154–157, 1995). Thus, it is not necessarily suitable to treat the contact lens by using these disinfectants.

Most of the conventional disinfectants for the contact lens are in the form of liquid, and are inconvenient in handling thereof. For instance, the user may spill the liquid disinfectant, and the fingers of the user may get wet by the spilled disinfectant. Further, the liquid disinfectant needs to be used for treating the contact lens in a limited place such as a bathroom where the spilled liquid disinfectant does not cause any trouble. In view of the above inconvenience experienced in using the conventional liquid disinfectant, it has been desired to provide an easy method of treating the contact lens.

SUMMARY OF THE INVENTION

It is therefore a first object of the present invention to provide a device for cleaning and disinfecting a contact lens that exhibits a high degree of disinfecting or sterilizing effect while assuring a high degree of safety, and that assures easy handling thereof.

It is a second object of the invention to provide a method of disinfecting a contact lens using the device as a disinfecting device.

The above first object of the present invention may be attained according to a first aspect of the invention which provides a device for cleaning and disinfecting a contact lens, the device including at least one treating portion which is brought into contact with the contact lens, wherein at least the at least one treating portion is formed of a water-absorbing solid soft material to which a disinfectant is fixed. The above first object of the invention may also be attained according to a second aspect of the invention which provides a device for disinfecting a contact lens having at least one disinfection treating portion formed of a water-absorbing solid soft material to which a disinfectant is fixed, the disinfectant disinfecting the contact lens which is brought into contact with and held by a surface of the soft material.

In the cleaning and disinfecting device for a contact lens, or the disinfecting device for a contact lens according to the present invention, the disinfectant fixed to the soft material kills the bacteria adhering to the surface of each treating portion of the device and the surface of the contact lens. Since the disinfectant fixed to the soft material is not separated or isolated therefrom, the disinfectant which would give an adverse influence on the eyes is not adsorbed on or stored in the contact lens. Thus, the cleaning and disinfecting device according to the present invention does not suffer from proliferation of the bacteria after it is used, and can be repeatedly used in a good sanitary condition. In addition, since the contact lens cleaned and disinfected by the cleaning and disinfecting device of the present invention does not suffer from the adsorption or storing of the disinfectant therein, the disinfectant is not emitted from the contact lens into the eye during wearing of the contact lens, eliminating a possibility of causing various troubles to the eyes. According to this arrangement, the contact lens can be cleaned and disinfected with safety.

In cleaning and disinfecting the contact lens, the present cleaning and disinfecting device in a solid form does not suffer from the various problems conventionally experienced in using the liquid agent, that is, the spilled liquid agent may soil the fingers of the user, for instance. Further, when the contact lens is cleaned and disinfected by using the present contact lens cleaning and disinfecting device, it is not required to pay great attention in treating the contact lens so as not to spill the liquid agent, as required when the conventional liquid agent is used. In contrast to the conventional liquid agent which needs to be used in a limited place where the spilled liquid agent does not cause any trouble, the present cleaning and disinfecting device can be used anywhere. Thus, the present cleaning and disinfecting device assures easy handling thereof.

In a first preferred form of the above first and second aspects of the present invention, the contact lens cleaning and disinfecting device includes a first member which has a receiving surface for receiving the contact lens and a second member which has a configuration corresponding to the receiving surface of the first member, the first and second members having respective contacting portions which are to be in contact with said contact lens, wherein at least the contacting portions of the first and second members are formed of the above-indicated water-absorbing solid soft material. The contact lens cleaning and disinfecting device of the present invention includes the first member having the contact lens receiving surface, and the second member having the configuration corresponding to the receiving surface of the first member. Further, each portion of the device with which the contact lens is brought into contact is formed of the solid soft material to which the disinfectant is fixed. In this arrangement, it is possible to simultaneously clean and disinfect the entire surface area of the contact lens by holding the contact lens to be treated by and between the first and second members. Accordingly, the present cleaning and disinfecting device assures easy cleaning and disinfection of the contact lens.

In a second preferred form of the above aspects of the present invention, the soft material is selected from the group consisting of homopolymers or copolymers of acrylic acid, polyvinyl alcohol, polyvinylformal and regenerated cellulose. These soft materials permit the disinfectant to be effectively fixed thereto, to thereby provide the cleaning and disinfecting device capable of effecting the cleaning and disinfection of the contact lens which is safe with respect to the eyes of the user. Further, since these soft materials have a sufficiently high degree of absorption of water and retention of water, a hydrogel or water-containing contact lens can be treated with high stability by the present cleaning and disinfecting device. When the hydrogel contact lens which is soft and is likely to deform is supported or held by the present device, the hydrogel contact lens does not suffer from any damage such as scratches on the surfaces thereof owing to a sufficiently low hardness of these soft materials.

In a third preferred form of the above aspects of the present invention, the disinfectant is selected from the group consisting of a guanidine disinfectant and a quaternary ammonium salt disinfectant. These disinfectants can be easily fixed to the soft material, and are not likely to separate therefrom. Moreover, these disinfectants have a wide range of antibacterial spectrum, so as to assure a high degree of disinfecting or sterilizing effect.

The above second object of the present invention may be attained according to a third aspect of the invention which provides a method of disinfecting a contact lens comprising the steps of: a) preparing a device for disinfecting a contact lens which has at least one disinfection treating portion formed of a water-absorbing solid soft material to which a disinfectant is fixed, b) impregnating at least the at least one disinfection treating portion of the device with a wetting agent, and c) contacting the contact lens with the at least one disinfection treating portion such that a surface of the contact lens to be disinfected is brought into contact with and held by the at least one disinfection treating portion. By impregnating the disinfection treating portion of the device with the wetting agent, the contact lens can be effectively brought into contact with the disinfection treating portion of the device. Further, this arrangement assures increased or stable contact of the disinfectant and the bacteria via the wetting agent, whereby the contact lens can be effectively disinfected.

In a first preferred form of the third aspect of the present invention, the wetting agent is a buffer.

In a second preferred form of the third aspect of the present invention, the wetting agent is a buffer which contains a surface active agent.

BRIEF DESCRIPTION OF THE DRAWINGS

The above and optional objects, features, advantages and technical significance of the present invention will be better understood by reading the following detailed description of presently preferred embodiments of the invention, when considered in conjunction of the accompanying drawings, in which:

FIG. 1A is an elevational view in cross section of a receptacle of the contact lens disinfecting device according to a first embodiment of the present invention, while

FIG. 2A is an elevational view in cross section of a cover of the contact lens disinfecting device according to the first embodiment of the present invention, while

DETAILED DESCRIPTION OF THE PREFERRED EMBODIMENTS

In the present invention, the contact lens is cleaned and disinfected by using the cleaning and disinfecting device which includes a predetermined treating portion or portions formed of a water-absorbing or water-absorbable soft material to which a predetermined disinfectant is fixed, so as to carry the disinfectant. The contact lens is disinfected safely in a simplified manner by using the cleaning and disinfecting device wherein at least the treating portion or portions are impregnated with a suitable wetting agent, such that the contact lens is brought into contact with and held by the treating portion or portions of the device for a predetermined time period.

For the purpose of assuring a high degree of safety as well as a high degree of disinfecting effect, the water-absorbing soft material used in the present invention is suitably selected so that the soft material permits a predetermined disinfectant to be chemically or physically fixed thereto, whereby the disinfectant fixed to the soft material does not easily separate or isolate therefrom. Since the soft material is brought into a direct contact with the contact lens, it is desirable that the soft material have a low degree of hardness which does not give any damage such as scratches on the surfaces of the contact lens. Further, the soft material preferably has retention of water for keeping the hydrogel contact lens with high stability. In view of the above requirements, the soft material to be used in the present invention is selected from among homopolymers or copolymers of acrylic acid, i.e., polyacrylic acid or copolymers of acrylic acid and at least one other vinyl monomer, polyvinyl alcohol, polyvinylformal and regenerated cellulose, for example. In particular, the polyvinyl alcohol and polyvinylformal are favorably used in the present invention since the polyvinyl alcohol and polyvinylformal homogeneously fix the disinfectant thereto. The soft material is preferably used in a porous form.

The disinfectant is chemically or physically fixed to the water-absorbing soft material as described above according to any known manner, provided that the disinfectant can be retained in the soft material without separating or isolating therefrom after it is fixed to the soft material. For instance, the disinfectant is fixed to the soft material under heat, in the following manner. Initially, the disinfectant is diluted to a suitable concentration, preferably in the concentration of 10 ppm–10000 ppm, more preferably 10 ppm–5000 ppm. In this diluted disinfectant, the soft material is soaked for a predetermined time period, preferably for a time period of from 10 minutes to 8 hours, more preferably for a time period of 30 minutes to 4 hours. After the soft material is soaked in the diluted disinfectant for the predetermined time period, the soft material may be used without being dried. In general, however, the soft material from which a redundant solution of the disinfectant has been removed is dried, or heated to a temperature of 85° C. for drying. Thus, the disinfectant is fixed to the soft material.

The disinfectant may be fixed to the soft material by using a coupling agent or a binder. For instance, the disinfectant is chemically bonded to the soft material by using a silane coupling agent.

The disinfectant may be fixed to the soft material either directly or indirectly.

For directly fixing the disinfectant to the soft material, the disinfectant is mixed with and dispersed in a raw material of which the soft material is formed, so that the disinfectant is fixed to the soft material at the same time when the soft material is produced. Alternatively, the disinfectant may be fixed to the formed soft material. In this case, the disinfectant is fixed to the soft material by contacting the soft material with a solution of the disinfectant, or by contacting the soft material with a solution of the disinfectant which contains a reaction aid, so as to selectively bond the disinfectant to the soft material owing to the reaction aid. One example of the method of directly fixing the disinfectant to the soft material owing to the reaction aid is described below. Namely, the soft material such as a polyvinylformal (PVF) sponge is immersed in a solution of a water-soluble salt generating a metal ion such as a 0.1–2.0 w/v% solution of NaCl, for a time period of from 30 minutes to 24 hours. After the soft material is taken out of the solution, a redundant solution is removed. Then, the soft material is immersed in a solution of polyhexamethylene biguanide hydrochloride salt (PHMB) or a solution of other cationic disinfectants such as chlorhexidine having a guanidine group, benzalkonium chloride and benzethonium chloride. If the PHMB solution is used, it has the concentration in a range as specified above. The soft material is immersed for a time period in a range also as specified above. The soft material may be left at room temperature while it is immersed in the disinfectant solution. However, if the soft material immersed in the disinfectant solution is kept at a temperature up to 60° C., the disinfectant can be fixed to the soft material in a reduced time period. Finally, a redundant disinfectant solution is removed from the soft material, whereby the disinfectant is fixed to the soft material.

For indirectly fixing the disinfectant to the soft material, the disinfectant and the coupling agent are mixed with a raw material of which the soft material is formed, so that the disinfectant is fixed to the soft material at the same time when the soft material is produced. Alternatively, the disinfectant may be fixed to the formed soft material. In this case, the soft material is brought into contact with a solution of the disinfectant containing the coupling agent, so that the disinfectant is fixed to the soft material.

It is not clear how the soft material and disinfectant are bonded after the disinfectant is fixed to the soft material. However, the soft material and disinfectant may be bonded in any way, as long as the disinfectant does not easily separate or isolate from the soft material after the disinfectant is fixed thereto. For instance, the disinfectant is fixed to the soft material so as to form an ionic bond therebetween. Preferably, the disinfectant is fixed to the soft material so as to form a covalent bond therebetween, which is stronger than the ionic bond.

The disinfectant to be suitably used in the present invention has a wide range of antibacterial spectrum. The disinfectant can be easily fixed to the water-absorbing soft material, and does not separate therefrom after it is fixed thereto. Examples of such a disinfectant are a quaternary ammonium salt disinfectant and a guanidine disinfectant. It is particularly preferable to employ the guanidine disinfectant, and the guanidine disinfectant in which a coupling group is introduced, such as: chlorhexidine, or chlorhexidine in which the coupling group is introduced; 1,17-diguanidino-9-aza-heptadecane, or 1,17-diguanidino-9-aza-heptadecane in which the coupling group is introduced; and polyhexamethylene biguanide, or polyhexamethylene biguanide in which the coupling group is introduced.

The contact lens is effectively cleaned by rubbing the surfaces thereof using the contact lens cleaning and disinfecting device wherein the predetermined disinfectant is fixed to at least its treating portions. Even if the bacteria adhere to, and remain in the contact lens cleaning and disinfecting device after it was used, the disinfectant fixed to the soft material kills the bacteria, thereby inhibiting or reducing proliferation of the bacteria while the cleaning and disinfecting device is stored. Accordingly, the present cleaning and disinfecting device is always kept clean, and can be repeatedly used in a good sanitary condition.

In the present method of cleaning and disinfecting the contact lens, the contact lens cleaning and disinfecting device as described above is used, which device including the treating portions formed of the water-absorbing solid soft material to which the disinfectant is fixed. The surfaces of the contact lens to be treated are held into contact with the treating portions (soft material) of the cleaning and disinfecting device with the device being impregnated with a wetting agent, so that the contact lens is cleaned and disinfected in a simplified manner with a significantly high degree of safety and a significantly enhanced sterilizing effect.

Described more specifically, the contact lens removed from the eye is rinsed with the wetting agent or a suitable storing agent as needed. In the meantime, the soft material which provides at least the treating portions of the cleaning and disinfecting device is impregnated with the wetting agent to a sufficient extent that the soft material is in a saturated condition. The contact lens is rubbed or held with the lens kept in contact with the soft material for a predetermined time period, so that the contact lens can be cleaned or disinfected as desired. The soft material used herein may take any form such as a sheet form, as long as the soft material has a shape or form which is capable of contacting with the contact lens to be disinfected.

Preferably, the soft material which provides at least the treating portions of the present cleaning and disinfecting device has a first member having a receiving surface for receiving the contact lens and a second member having a configuration corresponding to the receiving surface of the first member. The contact lens is held by and between the two members, so that the entire surface area of the contact lens is in contact with and held by the soft material to which the disinfectant is fixed. Accordingly, the entire surface area of the contact lens can be cleaned and disinfected at the same time, so as to facilitate the cleaning and disinfection of the contact lens.

Figure 1A:
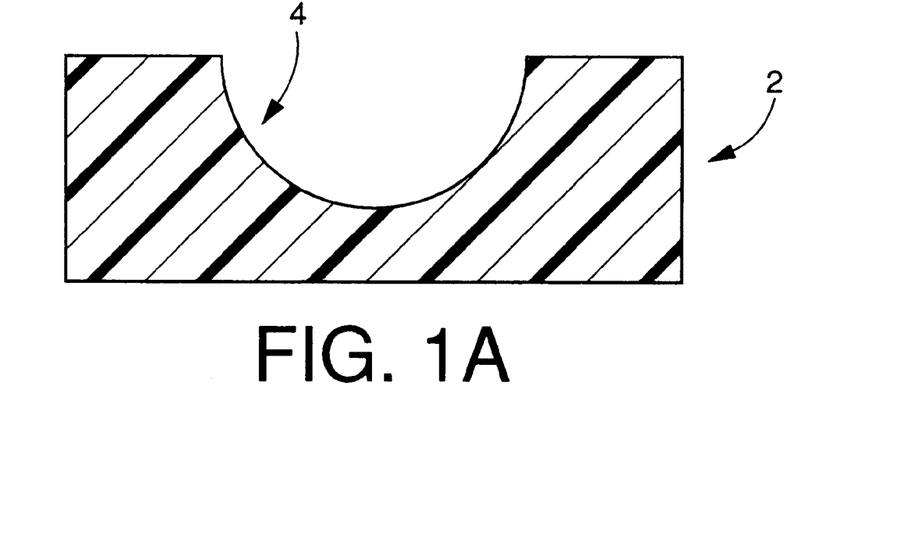
Figure 1B:
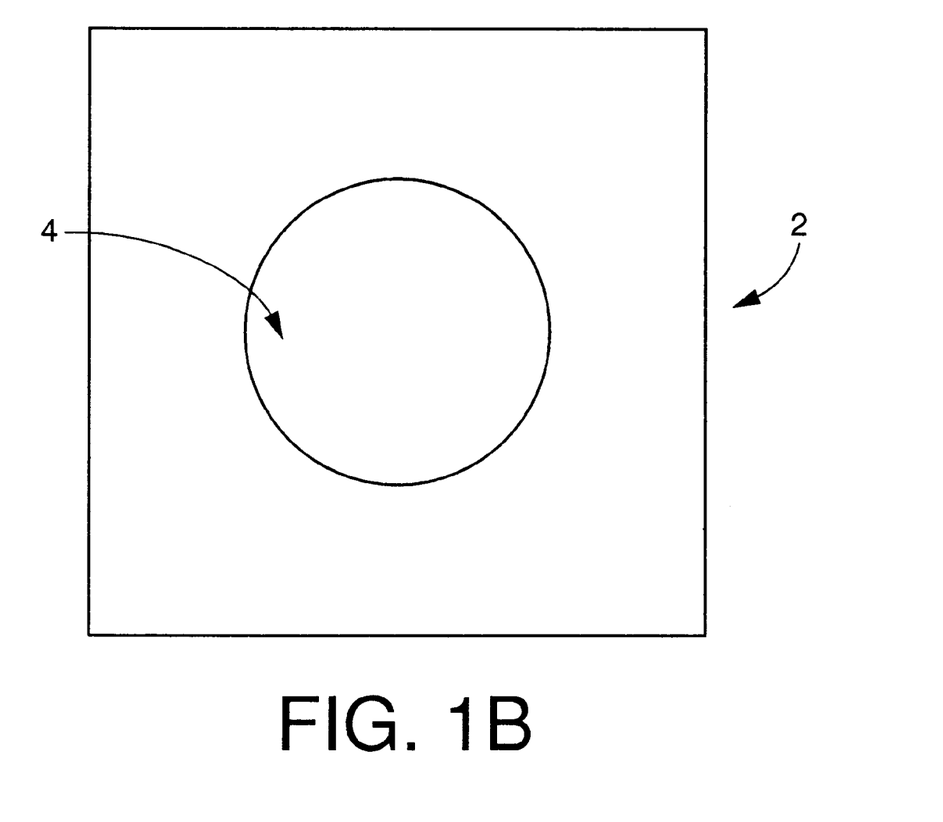
FIG. 1B is a plan view of the receptacle of FIG. 1A.

Referring first to FIGS. 1A and 1B, there is shown a first member in the form of a receptacle 2 constructed according to a first embodiment of the present invention. The receptacle 2 is a generally rectangular parallelopiped member, and formed of a water-absorbing soft material. The receptacle 2 includes a recess 4 serving as a disinfection treating portion and having a substantially spherical or elliptical surface on which the contact lens is placed. The radius of the recess 4 formed on the upper surface of the receptacle 2 and having the spherical or elliptical surface on which the contact lens is placed is not particularly limited as long as the radius corresponds to the radius of curvature of the ordinary contact lens. The radius of the recess 4 is generally in a range of 7.0 mm–9.5 mm, preferably in a range of 7.5 mm–9.0 mm. The thickness of the receptacle 2 is not particularly limited, provided that the receptacle 2 permits easy cleaning and disinfection of the contact lens and provides the recess 4 having a depth sufficient for receiving the contact lens.

Figure 2A:
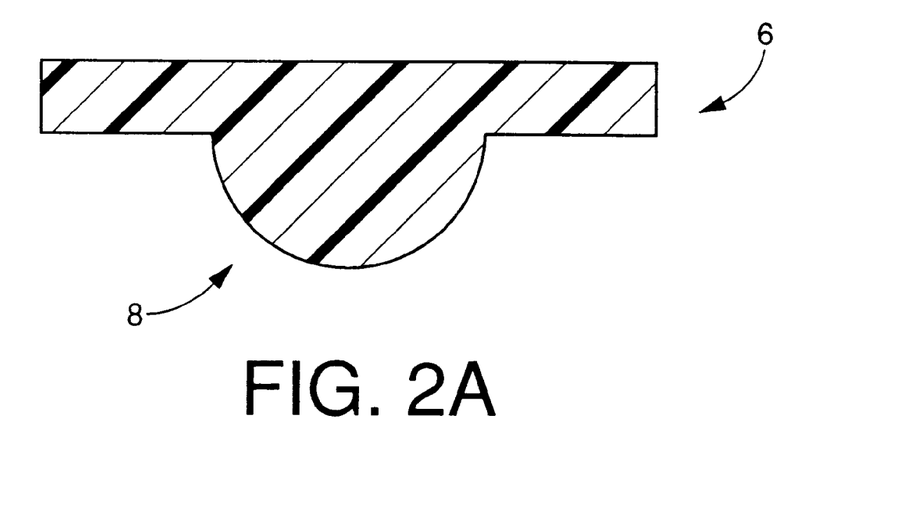
Figure 2B:
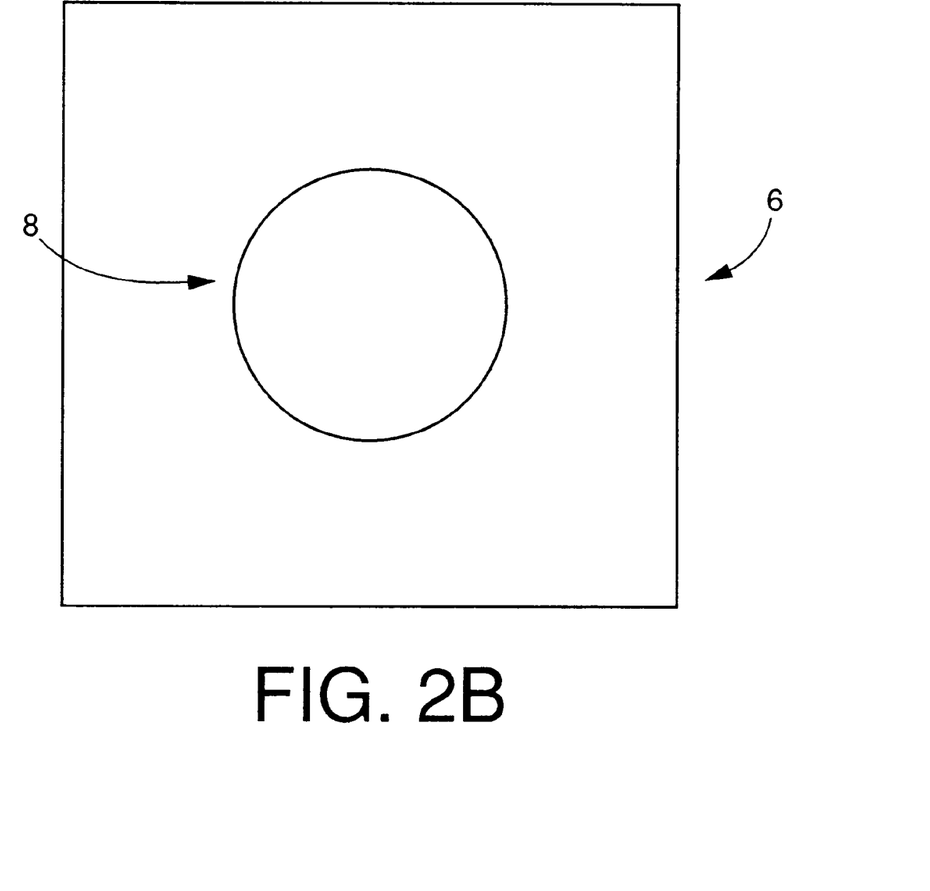
FIG. 2B is a bottom plan view of the cover of FIG. 2A.

Referring next to FIGS. 2A and 2B, there is shown a second member in the form of a cover 6 constructed according to the first embodiment of the present invention. Like the receptacle 2, the cover 6 is a generally rectangular parallelopiped member, and formed of the water-absorbing soft material. The cover 6 has a thickness which is slightly smaller than that of the receptacle 2. On the surface of the cover 6 which is to be opposed with the receptacle 2, there is formed a protrusion 8 serving as a disinfection treating portion. The protrusion 8 has a substantially spherical or elliptical surface corresponding to the configuration of the recess 4 of the receptacle 2. The radius of the protrusion 8 is made slightly smaller than that of the recess 4 of the receptacle 2. More specifically, the radius of the protrusion 8 is smaller than that of the recess 4 by 0.1 mm in the present embodiment. However, it is to be noted that the difference between the radii of the recess 4 and the protrusion 8 is not limited to the value in the present embodiment, but is suitably determined by taking account that the contact lens is held by and between the recess 4 and the protrusion 8.

Figure 3:
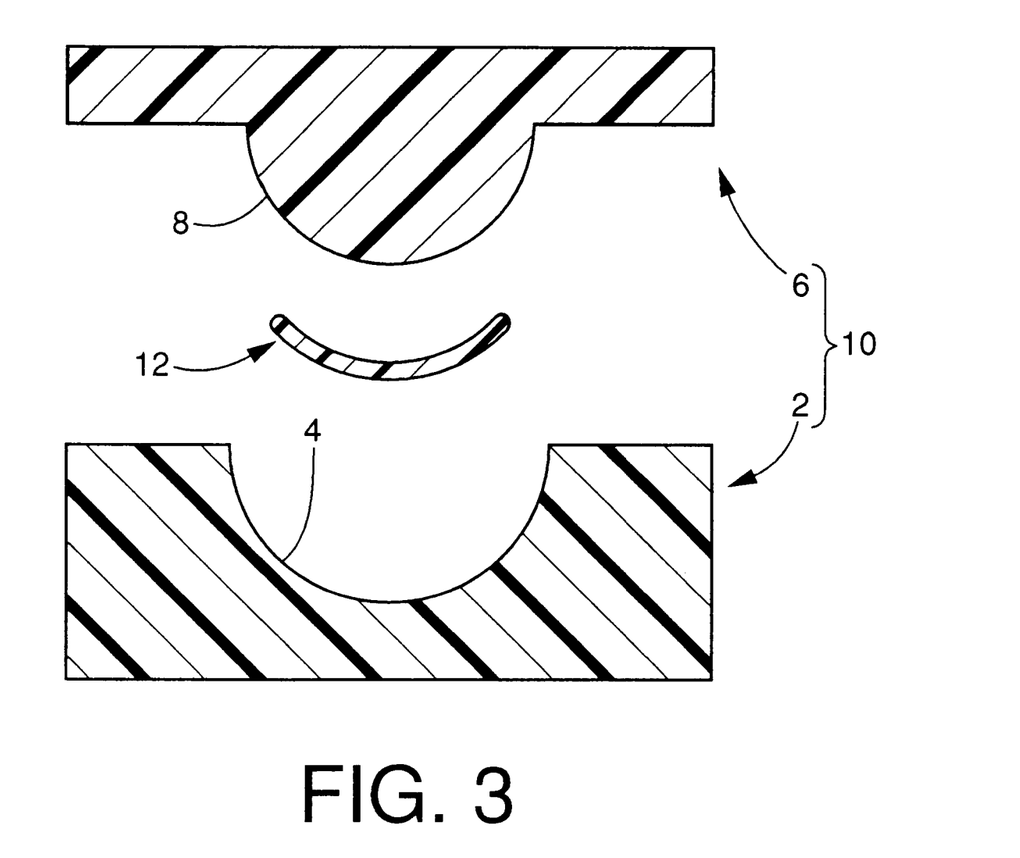
FIG. 3 is an elevational view in cross section of the contact lens disinfecting device according to the first embodiment of the invention, which includes the receptacle and the cover that are to be superposed on each other with a contact lens being interposed therebetween.

FIG. 3 shows a cleaning and disinfecting device 10 which includes the receptacle 2 and the cover 6 that are to be superposed on each other with a contact lens 12 interposed therebetween. In use, the contact lens cleaning and disinfecting device 10 consisting of the receptacle 2 and the cover 6 is initially impregnated with a wetting agent to a sufficient extent that the device 10 is in a saturated state. Then, the receptacle 2 is placed such that the recess 4 is to be opposed with the protrusion 8 of the cover 6 as shown in FIG. 3. The contact lens 12 to be cleaned and disinfected is placed in a central portion of the recess 4 such that the convex surface of the contact lens 12 is held in contact with the spherical or elliptical surface of the recess 4. Thereafter, the cover 6 is superposed on the receptacle 2 such that the protrusion 8 of the cover 6 is opposed to the recess 4 with the contact lens 12 interposed therebetween. According to this arrangement, the both surfaces of the contact lens are brought into contact with, rubbed and held by the soft material to which the disinfectant is fixed, whereby the entire surfaces of the contact lens can be cleaned and disinfected in a considerably simplified manner.

Figure 4:
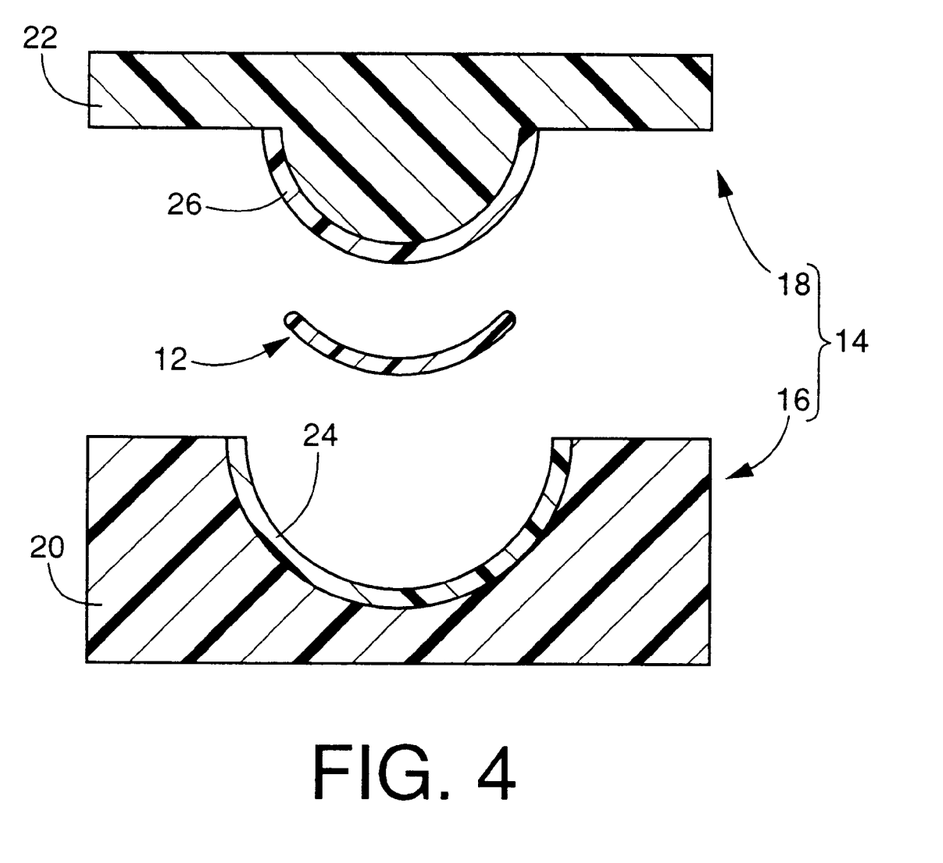
FIG. 4 is an elevational view in cross section of the contact lens disinfecting device according to a second embodiment of the invention, which includes the receptacle and the cover that are to be superposed on each other with a contact lens being interposed therebetween.

Referring next to FIG. 4, there is shown a contact lens cleaning and disinfecting device 14 according to a second embodiment of the present invention. As in the first embodiment, the contact lens cleaning and disinfecting device 14 of this second embodiment consists of two members, i.e., a receptacle 16 in the form of the first member and a cover 18 in the form of a second member. As shown in FIG. 4, the receptacle 16 includes a base 20 formed of a hard material such as plastic, and a sheet-type treating portion 24 bonded to a contacting surface of the base 20, which contacting surface is to be held in contact with the contact lens. Similarly, the cover 18 includes a base 22 formed of a hard material such as plastic, and a sheet-type treating portion 26 bonded to a contact lens contacting surface of the base 22. The sheet-type treating portions 24, 26 are formed of the water-absorbing soft material to which the disinfectant is fixed. In the present contact lens disinfecting device, at least the contacting surfaces (portions) which are to be in contact with the contact lens are formed of the soft material, so as to function as the disinfection treating portions.

The configuration of the contact lens cleaning and disinfecting device of the present invention is not limited to the configurations in the illustrated embodiments, but may be embodied with various changes, modifications and improvements, which may occur to those skilled in the art.

In the illustrated second embodiment of FIG. 4, the sheet-type soft materials are bonded to only the contact lens contacting surfaces of the base 20 of the receptacle 16 and the base 26 of the cover 18, respectively. However, the sheet-type soft materials may be bonded over the entire opposing surfaces of the base 20 and base 22.

The configuration of the recess of the receptacle which provides the contact lens receiving surface is not limited to the spherical or elliptical shape as in the illustrated embodiments. The recess of the receptacle may have a part-spherical or frustoconical shape, for instance. That is, the recess may have any configuration, as long as the contact lens is brought into contact with and held by the soft material to a sufficient extent by utilizing the shape of the protrusion formed so as to correspond to the shape of the receiving surface of the recess, and the flexibility of the soft material.

Unlike the receptacles and the covers in the illustrated embodiments, the receptacle may have a protrusion formed in its upper surface while the cover may have a recess formed in its lower surface.

Although each of the receptacle and cover in the illustrated embodiments is a generally rectangular parallelopiped member having a square bottom surface, the configuration of the receptacle and cover is not limited to that of the illustrated embodiments. For instances each of the receptacle and cover may be a generally cylindrical member having a circular bottom surface.

The first and second members may be integrally connected to each other by a suitable connecting member, to thereby assure easy handling of the disinfecting device.

Since the contact lens is usually used as one of a pair, the disinfecting device may be formed such that two contact lenses are disinfected at the same time. In this case, the disinfecting device has a pair of receptacles and a pair of covers for treating the two contact lenses.

In the illustrated embodiments, the contact lens cleaning and disinfecting device has two treating portions corresponding to the opposite surfaces of the contact lens. However, the cleaning and disinfecting device may have only a single treating portion corresponding to one of the opposite surfaces of the contact lens.

Any known wetting agents may be used in the present contact lens disinfecting device, provided that the wetting agent does not cause the separation of the disinfectant fixed to the soft material and it does not give an adverse influence on the material of the contact lens. As the wetting agent, purified water, distilled water or physiological salt solution is used. It is particularly preferable to use a buffer as the wetting agent. Any known buffers may be used as the wetting agent in the present invention, such as a borate buffer, a citrate buffer, a tris buffer or a phosphate buffer. Among these buffers, the borate buffer is particularly preferable since it provides an enhanced disinfecting effect. The borate buffer includes 2.0% of boric acid and 0.03% of borax, and has a pH of about 7.2, for example.

It is preferable that the buffer used as the wetting agent further contain a surface active agent. One example of the surface active agent to be contained in the buffer is a block polymer-type nonionic surface active agent which is formed by addition polymerization of ethylene oxide as a hydrophilic group, with polypropylene glycol as a lipophilic group obtained by polymerization of propylene oxide, such that the ethylene oxide is bonded to both ends of the polypropylene glycol. Examples of such a block polymer-type nonionic surface active agent are "Pluronic P123", "Pluronic P85", "PEP-101", "Pluronic F68" and "Pluronic F127" (all available from BASF CORPORATION, U.S.A.). Other examples of the non-ionic surface active agent are POE(60) hardened castor oil, POE(40) sorbitol tetraoleate and polyglycerin fatty acid ester.

When the buffer is used in combination with an ether-type nonionic surface active agent, it provides a sufficiently increased sterilizing effect owing to the combined use. Examples of such an ether-type nonionic surface active agent are: polyoxyethylene alkylphenylethers such as polyoxyethylene(5) nonylphenylether, polyoxyethylene (7.5) nonylphenylether, polyoxyethylene(10) nonylphenylether, polyoxyethylene(3) octylphenylether, and polyoxyethylene(10) octylphenylether; and polyoxyethylene alkylethers such as polyoxyethylene(7) cetylether and polyoxyethylene(9) laurylether. These surface active agents function as the wetting agent or penetrating agent. Since the surface active agent generally provides a cleaning effect, the contact lens can be cleaned at the same time owing to the addition of the surface active agent to the buffer as the wetting agent.

When the surface active agent having the cleaning effect is contained in the buffer, the following cleaning procedure is effected before, during or after the disinfecting treatment according to the present invention, whereby the contact lens can be cleaned and disinfected at the same time in a simplified manner. Described more specifically, as in the disinfecting method of the present invention, the contact lens is held by and between the receptacle 2 and the cover 6 of the disinfecting device 10 as described above. With the contact lens kept in contact with the two members, the cover 6 is slidably rotated with respect to the receptacle 2. According to this procedure, the opposite surfaces of the contact lens are rubbed between the contacting surfaces (portions) of the receptacle 2 and cover 6 of the disinfecting device 10, which contacting surfaces are provided by the soft material. Thus, the present contact lens cleaning and disinfecting device provides the same or even greater cleaning effect, as compared with the conventional finger-rubbing.

The wetting agent may further contain, as needed, any additional components such as a chelating agent, a tonicity agent, a preservative and a disinfectant, as long as they assure safety with respect to the living body without giving an adverse influence on the material of the contact lens. Each of these additional components is contained in the wetting agent in an amount that does not deteriorate the advantages provided by the present invention. As the chelating agent, sodium edetate, trihydroxymethylaminomethane, sodium polyphosphate, sodium pyrophosphate, sodium citrate, 1-hydroxyethane-1,1-diphosphonic acid or tetrasodium salt of 1-hydroxyethane-1,1-diphosphonic acid is used, for example. 25 Examples of the tonicity agent are sodium chloride, potassium chloride, sodium bicarbonate, polyhydric alcohols such as glycerin and propylene glycol, and saccharides such as glucose and mannitol. It is particularly preferable to use the glycerin and propylene glycol as the tonicity agent. The glycerin or propylene glycol is used in an amount that controls the osmotic pressure to about 300 mOsm. Examples of the preservative are Paraben (parahydroxybenzoic acid), basic nitrogen, sorbic acid, potassium sorbate, sodium benzoate, a guanidine preservative, and a quaternary ammonium salt preservative. As the disinfectant, chlorhexidine gluconate or thimerosal is used, for instance.

The wetting agent used in the present invention is easily prepared in a way as usually used for preparing an aqueous solution, without requiring any special procedure. Namely, the wetting agent is prepared by dissolving each component in a predetermined amount of purified water. The obtained wetting agent is subjected to a suitable sterilizing treatment such as sterile filtration, as needed.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention as defined in the attached claims.

Example 1

Specimens Nos. 1–3 of the contact lens disinfecting device were prepared in the following manner by respectively using, as the soft material, an unwoven fabric of acrylic acid copolymer, a polyvinylformal sponge, and a cellulose sponge, so as to examine whether these materials are suitable as the soft material.

Described more specifically, the specimens Nos. 1–3 of the contact lens disinfecting device consisting of the receptacle 2 and the cover 6 as shown in FIGS. 1A through 3 were prepared by respectively using, as the soft material, the unwoven fabric of acrylic acid copolymer, polyvinylformal sponge, and cellulose sponge. The receptacle 2 and cover 6 of each disinfecting device 10 were boiled in distilled water for 30 minutes. This boiling operation was repeated twice. Next, the disinfecting device 10 subjected to the boiling operation was immersed for one hour in a disinfectant solution, which is a solution of polyhexamethylene biguanide hydrochloride salt (PHMB) having a concentration of 1000 ppm. Thereafter, a redundant disinfectant solution was removed from the soft material which provides each disinfecting device 10. Then, the disinfecting device 10 was heated at the temperature of 75° C. so as to dry the soft material, whereby the disinfectant was fixed to the soft material. For assuring the reproducibility of the experiment, each of the dried soft materials to which the disinfectant was fixed (i.e., the disinfecting device 10) was subjected to an ultrasonic cleaning operation for 10 minutes in 300 mL of distilled water. This ultrasonic cleaning operation was repeated four times, by replacing the distilled water with a new one in each operation. Then, the soft material was again dried at 75° C. Thus, the specimens Nos. 1–3 of the contact lens disinfecting device were prepared.

In the meantime, there were prepared sample contact lenses 12 in the following manner. Initially a bacterium liquid including, as the test bacterium, Escherichia coli ATCC 8739 in an amount of $10^5$cfu/mL–$10^6$cfu/mL was prepared by using a physiological salt solution. In the thus prepared bacterium liquid, soft contact lenses ("MENICON SOFT MA" available from Menicon Co., Ltd., Japan) were immersed, to thereby provide the sample contact lenses 12 which were soiled with the bacteria adhering to the surfaces thereof.

The thus prepared sample contact lenses 12 were disinfected in the following manner by using the specimens Nos. 1–3 of the contact lens disinfecting device 10 in the dried state. Initially, each specimen was sufficiently impregnated with a physiological salt solution as a wetting agent. Then, the sample contact lens 12 was held by and between the recess 4 of the receptacle 2 and the protrusion 8 of the cover 6 of each specimen contact lens disinfecting device, so that the contact lens was kept in contact with the disinfecting device to a sufficient extent. Thereafter, the sample contact lens 12 kept in contact with the disinfecting device was stored in a thermostat kept at 25° C. for four hours, whereby the sample contact lens 12 was disinfected.

On the basis of the viable cell count of the Escherichia coli on the surface of each sample contact lens 12 before the disinfecting treatment and the viable cell count of the Escherichia coli on the surface of each sample contact lens 12 after the disinfecting treatment, there was calculated a rate of reduction of the Escherichia coli for each sample contact lens. The results are shown in the following TABLE 1.

TABLE 1

|  | Present invention | | |
|---|---|---|---|
|  | 1 | 2 | 3 |
| water-absorbing soft material | unwoven fabric of acrylic acid copolymer | polyvinyl-formal sponge | cellulose sponge |
| disinfectant | PHMB | PHMB | PHMB |
| reduction rate (%) | 94.0 | 99.1 | 84.7 |

It is confirmed from the above results that the contact lens disinfecting device specimens Nos. 1–3 according to the present invention exhibited a considerably high degree of sterilizing effect.

Example 2

The specimens Nos. 4–6 of the contact lens disinfecting device according to the present invention were prepared by using, as the disinfectant, chlorhexidine gluconate (CHG), silane coupling-type chlorhexidine gluconate (CHG-Si) and polyhexamethylene biguanide hydrochloride salt (PHMB), so as to examine whether they are suitable as the disinfectant to be used in the present invention. Each of the CHG, CHG-Si and PHMB was fixed to polyvinylformal (PVF) as the soft material as in the above Example 1, to thereby provide each of the specimens Nos. 4–6 of the contact lens disinfecting device.

The sample contact lenses prepared in the same manner as in the Example 1 were disinfected by using the specimens Nos. 4–6 of the contact lens disinfecting device in the dried state, as in the Example 1.

On the basis of the number of the Escherichia coli adsorbed on each sample contact lens 12 before the disinfecting treatment and the viable cell count of the Escherichia coli in each sample contact lens 12 after the disinfecting treatment, there was calculated a rate of reduction of the Escherichia coli for each sample contact lens. The results are shown in the following TABLE 2.

TABLE 2

|  | Present invention | | |
|---|---|---|---|
|  | 4 | 5 | 6 |
| water-absorbing soft material | PVF | PVF | PVF |
| disinfectant | CHG | CHG-Si | PHMB |
| reduction rate (%) | 93.8 | 96.0 | 99.2 |

It was confirmed from the above results that the specimens Nos. 4–6 of the contact lens disinfecting device according to the present invention exhibited a sufficiently high degree of sterilizing effect.

Example 3

To examine the sterilizing effect of a sheet-type soft material to which the disinfectant is fixed, the following test was conducted. Initially, there was prepared a soft material to which the disinfectant is fixed as in the above Example 1, by using polyvinylformal (PVF) as the soft material and PHMB as the disinfectant. The thus obtained soft material was cut into a plurality of sheets each having a size of 2×20×50 mm. The thus obtained sheet-type soft material (hereinafter referred to as "PVF sheet") was used as a specimen No. 7 according to the present invention. In the meantime, there was prepared a soft material to which the disinfectant was not fixed. This soft material was cut into a plurality of sheets, so that the obtained sheet-type soft material (PVF sheet) was used as a specimen No. 1 according to a comparative example.

There were prepared three kinds of bacteria liquids which contain, as the test bacteria, E.C. (Escherichia coli ATCC 8739), P.a. (Pseudomonas aeruginosa ATCC 9027) and S.a. (Staphylococcus aureus ATCC 6538P), respectively. 2.5 mL of each bacteria liquid was applied to the PVF sheets of the specimen No.7 according to the present invention and the PVF sheets of the specimen No. 1 according to the comparative example, respectively. After the PVF sheets to which the bacteria liquids were applied were stored at 25° C. for two hours, the bacteria liquids were collected from the PVF sheets. Then, there was measured a viable cell count for each of the collected bacteria liquids. The results are shown in TABLE 3. Each of the PVF sheets from which the bacteria liquids had been collected was cultured in a bouillon medium which contains SCDLP (soybean-casein-digest-lecithin-Polysorbate 80: an inactivating agent), so as to examine whether any bacteria remained in each PVF sheet. The results are shown in TABLE 4.

TABLE 3

| | initial viable cell count | viable cell count after storage | |
|---|---|---|---|
| | | Present invention 7 | Comparative example 1 |
| test bacteria | | | |
| E.c. | $4.8 \times 10^4$ | 0 | $4.3 \times 10^4$ |
| P.a. | $1.2 \times 10^4$ | 0 | $1.1 \times 10^4$ |
| S.a. | $2.8 \times 10^4$ | 0 | $2.9 \times 10^4$ | unit: cfu/mL

TABLE 4

| | bacteria remaining in the PVF sheets | |
|---|---|---|
| | Present invention 7 | Comparative example 1 |
| test bacteria | | |
| E.c. | not found | found |
| P.a. | not found | found |
| S.a. | not found | found |

It will be apparent from the above results that the water-absorbing solid soft material to which the disinfectant is fixed exhibited an excellent sterilizing effect even when it was used in the sheet form.

Example 4

A test for checking the sterilizing effect of the present contact lens disinfecting device was conducted in the following manner by using the soft material, disinfectant and wetting agent in combination as indicated in TABLE 5. The test was conducted to examine: 1) the difference between the sterilizing efficacy of a soft material (PVF) to which a disinfectant (PHMB) is fixed, and that of a soft material (PVF) to which a disinfectant (PHMB) is not fixed, and 2) the influence of the wetting agent on the sterilizing effect when a physiological salt solution, and a physiological salt solution containing a borate buffer were used as the wetting agent.

As in the above Example 1, sample contact lenses were prepared by using, the test bacteria, E.c. (Escherichia coli ATCC 8739), P.a. (Pseudomonas aeruginosa ATCC 9027) and S.a. (Staphylococcus aureus ATCC 6538P), respectively. Next, specimens Nos. 8–9 of the contact lens disinfecting device according to the present invention were prepared by using the soft material and disinfectant in combination as indicated in the TABLE 5. As comparative examples, there were prepared specimens Nos. 2 and 3 of the contact lens disinfecting device, wherein the soft material was heated and dried without being immersed in the disinfectant, so that the disinfectant is not fixed to the obtained specimens according to the comparative examples.

In the same manner as in the above Example 1, the sample contact lenses were disinfected by using the specimens of the contact lens disinfecting device prepared as described above. In the specimen No. 8 according to the present invention and the specimen No. 2 according to the comparative example, the physiological salt solution was used as the wetting agent, while, in the specimen No. 9 according to the present invention and the specimen No. 3 according to the comparative example, the borate buffer was used as the wetting agent.

On the basis of the viable cell count of each of the test bacteria in the sample contact lenses before the disinfecting treatment and the viable cell count of each of the test bacteria in the sample contact lenses after the disinfecting treatment, there was calculated a rate of reduction of each of the test bacteria. The results are shown in the following TABLE 5.

TABLE 5

| | Present invention | | Comparative examples | |
|---|---|---|---|---|
| | 8 | 9 | 2 | 3 |
| water-absorbing soft material | PVF | PVF | PVF | PVF |
| disinfectant | PHMB | PHMB | — | — |
| wetting agent | | | | |
| concentration of NaCl (%) | 0.49 | 0.49 | 0.49 | 0.49 |
| concentration of borate (%) | — | 0.90 | — | 0.90 |
| reduction rate | | | | |
| E.c. (%) | 99.0 | 100 | 2.2 | 7.1 |
| P.a. (%) | 87.5 | 100 | 1.8 | 10.0 |
| S.a. (%) | >99.9 | 100 | 0.7 | 8.1 |

As is apparent from the above results, the contact lens can be effectively disinfected by using the disinfecting device to which the disinfectant is fixed. In addition, it was confirmed that the use of the borate buffer as the wetting agent can assure further enhanced disinfecting effect.

Example 5

For checking the safety of the present contact lens disinfecting device, the following test was conducted so as to examine the presence of the disinfectant separated from the soft material. As in the above Example 1, there was prepared a specimen No.10 of the contact lens cleaning device according to the present invention by using polyvinylformal as the soft material and polyhexamethylene biguanide hydrochloride salt as the disinfectant. The obtained specimen was saturated with distilled water.

As a comparative example, a specimen No. 4 of the contact lens disinfecting device was prepared such that polyvinylformal as the soft material was simply dried without being immersed in the disinfectant (the polyhexamethylene biguanide hydrochloride salt). Therefore, the disinfectant is not fixed to the soft material of the specimen No. 4 of the comparative example. The thus obtained specimen was saturated with distilled water.

Each specimen prepared as described above was airtightly accommodated in a Petri-dish so as to prevent evaporation of the aqueous component, and kept at 25° C. for five hours. Thereafter, the distilled water was collected from each specimen, to thereby provide a test solution.

Each test solution was inspected for the presence of the polyhexamethylene biguanide hydrochloride salt by observing absorption at about 236 nm by a spectrophotometer. No absorption was observed at 236 nm in the test solution of the specimen No. 10 according to the present invention and the test solution of the specimen No. 4 according to the comparative example. This indicates that the disinfectant fixed to the soft material was not separated or isolated therefrom into the wetting agent and adsorbed on the contact lens. Thus, the test shows that the contact lens can be disinfected with a high degree of safety according to the present disinfecting method.

Example 6

For checking the safety of the contact lens disinfecting device according to the present invention, a test was conducted to measure the inhibitory rate of proliferation of animal cells. Initially, there were prepared test solutions by collecting the distilled water from the specimen No. 10 according to the present invention and the specimen No. 4 according to the comparative example, respectively, as in the above Example 5. There was prepared a liquid agent (i.e., a cleaning, disinfecting and storing liquid which contains 0.5 $\mu$g/mL of polyhexamethylene biguanide hydrochloride salt). This liquid agent is capable of functioning as a cleaning, disinfecting and storing liquid, and can be applied to the eye during wearing of the contact lens. The liquid agent is commercially available and highly evaluated abroad. This liquid agent was used as a test solution of a specimen No. 5 according to a comparative example.

Next, each of the specimens of the test solution prepared as described above and, as a control, phosphate buffer without containing $Ca^{2+}$ and $Mg^{2+}$ [PBS (–)] were added to single-layer fibroblasts of a mouse which were subjected to tissue cultivation on 96 well microplates, in an amount of 10% with respect to the medium. These microplates were cultured in an incubator of 5% $CO_2$ kept at 37° C. for three days. According to the protein-quantitative analysis method (Lowry method: J.Biol.Chem., 193,265,1951), the absorption (OD) at 650 nm was measured by using an amount of proliferated cells as an amount of protein. Then, the proliferation inhibitory rate of each specimen with respect to the cells was calculated according to the following equation. The results are shown in TABLE 6.

proliferation inhibitory rate (%) =
{(the OD of the PBS(–) – the OD of each test solution)/ the OD of the PBS(–)} × 100

TABLE 6

|  | Present invention | Comparative examples | |
| --- | --- | --- | --- |
|  | 10 | 4 | 5 |
| proliferation inhibitory rate (%) | 7.2 | 8.6 | 38.0 |

It was confirmed from the above results that the contact lens disinfecting device according to the present invention is capable of assuring safety which is considerably higher than the liquid agent commercially available and highly evaluated abroad.

Example 7

A test for checking the sterilizing effect of the present contact lens disinfecting device was conducted by using a disinfecting device which had been stored under a high temperature for a long period of time, so as to confirm whether the disinfecting device can maintain high stability over a long period of time.

Initially, sample contact lenses were prepared in the same manner as in the above Example 1, by using, as the test bacteria, E.c. (Escherichia coli ATCC 8739), P.a. (Pseudomonas aeruginosa ATCC 9027) and S.a. (Staphylococcus aureus ATCC 6538P), respectively. As in the above Example 4, there were prepared a specimen No. 11 of the contact lens disinfecting device according to the present invention formed of the soft material (PVF) to which the disinfectant (PHMB) was fixed, and a specimen No. 6 of the contact lens disinfecting device according to a comparative example formed of the soft material (PVF) to which the disinfectant (PHMB) was not fixed. The specimen No 11 according to the present invention was stored under the temperature of 50° C. for 60 days.

The sample contact lenses were disinfected in the same manner as in the above Example 1, by using the specimens of the contact lens disinfecting device prepared as described above. As the wetting agent, the borate buffer containing the physiological salt solution as used in the above Example 4 was used.

On the basis of the viable cell count of each of the test bacteria on the surfaces of the sample contact lenses before the disinfecting treatment and the viable cell count of each of the test bacteria on the surfaces of the sample contact lenses after the disinfecting treatment, there was obtained a rate of reduction of each of the bacteria. The results are indicated in the following TABLE 7.

TABLE 7

|  | Present invention 11 | Comparative example 6 |
| --- | --- | --- |
| water-absorbing soft material | PVF | PVF |
| disinfectant | PHMB | — |

TABLE 7-continued

|  | Present invention 11 | Comparative example 6 |
|---|---|---|
| reduction rate | | |
| E.c. (%) | 100 | 2.0 |
| P.a. (%) | 100 | 1.5 |
| S.a. (%) | 100 | 0.3 |

As is apparent from the above results, it was confirmed that the contact lens disinfecting device according to the present invention maintained a considerable high sterilizing efficacy even after it was stored under the severe condition for a long period of time.

Example 8

A test for checking the cleaning effect of the present contact lens cleaning and disinfecting device was conducted in the following manner.

Initially, a solution of an artificial lipid to be used in the test was prepared in the following manner. There were dissolved 6 w/v% of sorbitan monooleate, 16 w/v% of castor oil, 35 w/v% of lanolin, 5 w/v% of oleic acid, 4 w/v% of sorbitan trioleate, 2 w/v% of cetyl alcohol, 2 w/v% of cholesterol and 30 w/v% of cholesterol acetate. The obtained mixture was agitated so as to provide a homogeneous liquid of an artificial lipid. 2.5 parts of the obtained artificial lipid liquid were mixed with 97.5 parts of a physiological salt solution, to thereby provide the solution of the artificial lipid.

As a sample contact lens, a soft contact lens ("MENICON SOFT MA" available from Menicon Co., Ltd., Japan) was prepared. Each of the surfaces of the contact lens was uniformly coated with 5 $\mu$L of the artificial lipid solution prepared as described above, so that the surfaces of the contact lens were stained with the artificial lipid.

A sample of the contact lens cleaning and disinfecting device was prepared as in the above Example 1 by using the PVF as the soft material and the PHMB as the disinfectant. The obtained sample was sufficiently impregnated with a wetting agent of a borate buffer which contains 0.5% of polyoxyethylene(10) nonylphenylether as an ether-type non-ionic surface active agent. The contact lens whose surfaces are stained with the artificial lipid was held by and between the recess of the receptacle and the protrusion of the cover of the sample cleaning and disinfecting device prepared as described above, so that the contact lens was kept in contact with the cleaning and disinfecting device. In this state, the cover and the receptacle are slidably rotated with each other, so that the contact lens was subjected to the cleaning operation for ten seconds.

The surfaces of the contact lens was observed after the cleaning operation, and it was confirmed that the artificial lipid adhering to the surfaces of the contact lens was completely removed therefrom. It is apparent from the result that the contact lens cleaning and disinfecting device according to the present invention is capable of exhibiting an excellent cleaning effect as well as an excellent sterilizing effect.

Example 9

The following test was conducted to examine the difference between the sterilizing efficacy of a soft material impregnated with a wetting agent prepared as described below, and that of the wetting agent per se.

The wetting agent to be used in this Example was prepared so as to have the composition below:

| propylene glycol | 1.48 | w/v % |
| sodium pyrophosphate (10H$_2$O) | 0.0838 | w/v % |
| boric acid | 0.5 | w/v % |
| Pluronic F-127 | 0.2 | w/v % |

The thus prepared wetting agent had a pH of 7.2 and an osmotic pressure of 300 mmol/kg.

Next, there were prepared three kinds of test liquids by mixing the wetting agent prepared as described above and each of the following three test bacteria in an amount described below, respectively:

| S. marcescens (ATCC 13880) | 5.3 × 10$^5$ cfu/ml |
| P. aeruginosa (ATCC 9027) | 1.3 × 10$^6$ cfu/ml |
| S. aureus (ATCC 6538) | 1.5 × 10$^6$ cfu/ml |

A polyvinylformal (PVF) sponge to which the disinfectant (PHMB) had been fixed were sterilely cut into a plurality of sheets each having a size of 20×50×2.0 mm. Each of the PVF sheet was subjected to an ultraviolet sterilizing treatment so that each surface of the PVF sheet was irradiated with the ultraviolet rays for 30 minutes.

The PVF sheets were impregnated with about 2.5 ml of the respective test liquids prepared as described above, so that the PVF sheets were saturated with the test liquids. Then, each of the PVF sheets was air-tightly accommodated in a Petri-dish so as to prevent evaporation of the aqueous component, and stored in an incubator kept at 25° C. for 4 hours. Thereafter, the test liquids were collected from the PVF sheets. Then, there was measured a viable cell count for each of the collected test liquids according to a poured plate method using an SCDLP medium that contains, as an inactivating agent, lecithin and Polysorbate 80. Similarly, there was measured a viable cell count for each of the test liquids each consisting of the wetting agent and each of the bacteria as described above. The results are indicated in the following TABLE 8.

TABLE 8

| | PVF sheets impregnated with the wetting agent | | wetting agent per se | |
|---|---|---|---|---|
| | viable cell count (cfu/ml) | reduction rate (%) | viable cell count (cfu/ml) | reduction rate (%) |
| test bacteria | | | | |
| S.m. | 1.4 × 10$^3$ | 99.7 | 4.5 × 10$^5$ | 15.1 |
| P.a. | 1.0 × 10$^2$ | 99.992 | 2.6 × 10$^5$ | 80.0 |
| S.a. | 1.1 × 10$^3$ | 99.92 | 8.3 × 10$^5$ | 44.7 |

It is clear from the above results that the sterilizing efficacy is significantly high when the wetting agent is used in combination with the soft material.

In the present contact lens cleaning and disinfecting device, the contact lens is disinfected with the lens being kept in contact with, and held by the disinfection treatment portions of the device formed of the soft material to which the disinfectant is fixed. According to this arrangement, the contact lens can be disinfected by the disinfectant having a high sterilizing effect. In addition, since the disinfectant is fixed to the soft material, the sterilizing component of the disinfectant which is harmful to the eyes is not adsorbed on and stored in the contact lens, so that the present contact lens cleaning and disinfecting device assures further enhanced safety with respect to the eyes.

In the present invention, the disinfecting device in a solid form is used for disinfecting the contact lens, eliminating the problems experienced when the conventional liquid agent is used to disinfect the contact lens. For instance, the liquid agent may be spilled during the disinfecting treatment, so that the fingers of the users may be soiled with the spilled liquid agent. Unlike the conventional liquid agent which needs to be used in a limited place such as a bathroom, the present disinfecting device can be used anywhere. Since the present disinfecting device employs a chemical disinfecting method, it does not require any boiling apparatus or electric power source for driving the boiling apparatus usually required in a thermal disinfecting method. Thus, the present disinfecting device permits the contact lens to be disinfected in a significantly simplified manner.

What is claimed is:

1. A device for cleaning and disinfecting a contact lens, said device including at least one disinfection treating portion that is brought into contact with said contact lens, wherein at least said one treating portion is formed of a water-absorbing solid soft material to which a disinfectant is chemically or physically fixed, so that said disinfectant is retained in said soft material without separation or isolation therefrom after said disinfectant is fixed to said soft material.

2. A device for cleaning and disinfecting a contact lens according to claim 1, including a first member which has a receiving surface for receiving said contact lens and a second member which has a configuration corresponding to said receiving surface of said first member, said first and second members having respective contacting portions which are to be in contact with said contact lens, wherein said at least one treating portion consists of said respective contacting portions of said first and second members.

3. A device for cleaning and disinfecting a contact lens according to claim 1, wherein said soft material is selected from the group consisting of homopolymers or copolymers of acrylic acid, polyvinyl alcohol, polyvinylformal and regenerated cellulose.

4. A device for cleaning and disinfecting a contact lens according to claim 1, wherein said disinfectant is selected from the group consisting of a guanidine disinfectant and a quaternary ammonium salt disinfectant.

5. A device for cleaning and disinfecting a contact lens according to claim 1, wherein said water-absorbing solid soft material is porous.

6. A device for disinfecting a contact lens having at least one disinfection treating portion formed of a water-absorbing solid soft material to which a disinfectant is chemically or physically fixed, so that said disinfectant is retained in said soft material without separation or isolation therefrom after said disinfectant is fixed to said soft material, said disinfectant disinfecting said contact lens which is brought into contact with and held by a surface of said soft material.

7. A device for cleaning and disinfecting a contact lens according to claim 6, including a first member which has a receiving surface for receiving said contact lens and a second member which has a configuration corresponding to said receiving surface of said first member, said first and second members having respective contacting portion which are to be in contact with said contact lens, wherein said at least one disinfection treating portion consists of said respective contacting portions of said first and second members.

8. A device for cleaning and disinfecting a contact lens according to claim 6, wherein said soft material is selected from the group consisting of homopolymers or copolymers of acrylic acid, polyvinyl alcohol, polyvinylformal and regenerated cellulose.

9. A device for cleaning and disinfecting a contact lens according to claim 6, wherein said disinfectant is selected from the group consisting of a guanidine disinfectant and a quaternary ammonium salt disinfectant.

10. A device for cleaning and disinfecting a contact lens according to claim 6, wherein said water-absorbing solid soft material is porous.

11. A method of disinfecting a contact lens comprising the steps of:

preparing a device for disinfecting a contact lens that has at least one disinfection treating portion formed of a water-absorbing solid soft material to which a disinfectant is chemically or physically fixed, so that said disinfectant is retained in said soft material without separation or isolation therefrom after said disinfectant is fixed to said soft material, impregnating at least said at least one disinfection treating portion of said device with a wetting agent, and contacting said contact lens with said at least one disinfection treating portion such that a surface of said contact lens to be disinfected is brought into contact with and held by said at least one disinfection treating portion.

12. A method of disinfecting a contact lens according to claim 11, wherein said wetting agent is a buffer.

13. A method of disinfecting a contact lens according to claim 11, wherein said wetting agent is a buffer which contains a surface active agent.

14. A method of disinfecting a contact lens according to claim 13, wherein said surface active agent is another-type nonionic surface active agent.

15. A method of disinfecting a contact lens according to claim 11, wherein said device for disinfecting said contact lens includes a first member which has a receiving surface for receiving said contact lens and a second member which has a configuration corresponding to said receiving surface of said first member, said first and second members having respective contacting portions which are to be in contact with said contact lens, wherein said at least one disinfection treating portion consists of said respective contacting portions of said first and second members.

16. A method of disinfecting a contact lens according to claim 11, wherein said soft material is selected from the group consisting of homopolymers or copolymers of acrylic acid, polyvinyl alcohol, polyvinylformal and regenerated cellulose.

17. A method of disinfecting a contact lens according to claim 11, wherein said disinfectant is selected from the group consisting of a guanidine disinfectant and a quaternary ammonium salt disinfectant.

18. A method of disinfecting a contact lens according to claim 11, wherein said water-absorbing solid soft material is porous.

19. A device according to claim 1, wherein said disinfectant is fixed to said soft material by an ionic or a covalent bond therebetween.

20. A device according to claim 1, wherein said disinfectant is fixed to said soft material by mixing said disinfectant with and dispersing said disinfectant in a raw material of which said soft material is formed.

21. A device according to claim 6, wherein said disinfectant is fixed to said soft material by an ionic or a covalent bond therebetween.

22. A device according to claim 6, wherein said disinfectant is fixed to said soft material by mixing said disinfectant with and dispersing said disinfectant in a raw material of which said soft material is formed.

23. A method according to claim 11, wherein said disinfectant is fixed to said soft material by an ionic or a covalent bond therebetween.

24. A method according to claim 11, wherein said disinfectant is fixed to said soft material by mixing said disinfectant with and dispersing said disinfectant in a raw material of which said soft material is formed.

* * * * *